United States Patent [19]
Kennis et al.

[11] Patent Number: 6,103,725
[45] Date of Patent: Aug. 15, 2000

[54] ALKYLAMINOBENZOTHIAZOLE AND -BENZOXAZOLE DERIVATIVES

[75] Inventors: Ludo Edmond Josephine Kennis, Turnhout; Josephus Carolus Mertens, Oud-Turnhout; Serge Maria Aloysius Pieters, Antwerp, all of Belgium

[73] Assignee: Janssen Pharmaceutica, N.V., Beerse, Belgium

[21] Appl. No.: 09/180,369

[22] PCT Filed: May 2, 1997

[86] PCT No.: PCT/EP97/02505

§ 371 Date: Nov. 9, 1998

§ 102(e) Date: Nov. 9, 1998

[87] PCT Pub. No.: WO97/43271

PCT Pub. Date: Nov. 20, 1997

[30] Foreign Application Priority Data

May 10, 1996 [EP] European Pat. Off. .............. 96201282

[51] Int. Cl.[7] ..................... A61K 31/496; C07D 413/12; C07D 417/12
[52] U.S. Cl. .................. 514/254.02; 544/368; 424/1.11; 424/1.37; 435/7.1
[58] Field of Search ............................... 544/368; 514/253

[56] References Cited

U.S. PATENT DOCUMENTS 5,164,397 11/1992 Pascal et al. ............................. 514/275
5,731,438 3/1998 Cook et al. .............................. 544/368

FOREIGN PATENT DOCUMENTS 0 335 586 3/1988 European Pat. Off. .
0 435 749 12/1990 European Pat. Off. .

OTHER PUBLICATIONS

Van Toc et al, *Nature*, vol. 350, p. 610–614 (1991).
TenBrink et al., J.Med.Chem., vol. 39, p.2435–2437, 1996.
Chimioca Therapeutica, vol. VIII, No. 6, Nov. 1973, Paris, FR. pp. 655–658 "Bases de Manich Derivees d' Amino–2 Benzothiazoles:etude des Activites Analagestiques et Anti-inflammatoire".

*Primary Examiner*—Emily Bernhardt
*Attorney, Agent, or Firm*—Mary A. Appollina

[57] ABSTRACT

The present invention concerns the compounds of formula

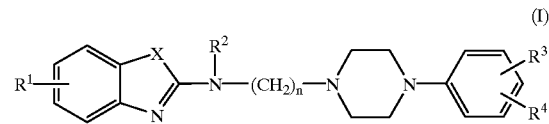

(I)

the N-oxide forms, the pharmaceutically acceptable acid addition salts and stereochemically isomeric forms thereof, wherein X is O or S; n is 2, 3, 4 or 5; $R^1$ is hydrogen, $C_{1-6}$alkyl, $C_{1-6}$alkyloxy or halo; $R^2$ is hydrogen, $C_{1-6}$alkyl, phenyl, phenyl$C_{1-6}$alkyl or phenylcarbonyl; $R^3$ and $R^4$ each independently are selected from hydrogen, halo, nitro, $C_{1-6}$alkyl, $C_{1-6}$alkyloxy, halo$C_{1-6}$alkyl, aminosulfonyl, mono- or di($C_{1-4}$alkyl)aminosulfonyl; or $R^3$ and $R^4$ may also be taken together to form a bivalent radical of formula —CH=CH—CH=CH—; it further relates to processes for their preparation, compositions comprising them as well as their use as a medicine; compounds of formula (I) containing a radioactive isotope; a process of marking dopamine $D_4$ receptor sites; and a process for imaging an organ are disclosed.

10 Claims, No Drawings

ALKYLAMINOBENZOTHIAZOLE AND -BENZOXAZOLE DERIVATIVES

CROSS REFERENCE TO RELATED APPLICATIONS

This application is a National Stage application under 35 U.S.C. § 371 of PCT/EP97/02505 filed May 2, 1997, which claims priority from EP 96.201.282.9, filed May 10, 1996.

The present invention concerns alkylaminobenzothiazoles and -benzoxazoles; it further relates to processes for their preparation, compositions comprising them, as well as their use as a medicine. The compounds of the present invention exhibit specific dopamine $D_4$ receptor antagonism and may particularly be useful as antipsychotics, especially in the treatment and/or prevention of psychotic disorders such as schizophrenia. In addition, the present invention concerns compounds of formula (I) containing a radioactive isotope; a process of marking dopamine $D_4$ receptor sites; and a process for imaging an organ.

It is generally accepted knowledge that dopamine receptors are important for many biochemical functions in the animal body. For example, altered functions of these receptors not only participate in the genesis of psychosis, but also of anxiety, emesis, motoric functions, addiction, sleep, feeding, learning, memory, sexual behaviour, regulation of immunological responses and blood pressure. Since dopamine receptors control a great number of pharmacological events, some of which are thus far unknown, there is a possibility that compounds which exhibit a specific binding affinity for the $D_4$ receptor may exert a wide range of therapeutic effects in humans.

EP-A-0,335,586, published on Oct. 4, 1989, describes 2-[4-(diarylmethyl)-1-piperazinyl)alkylamino]benzothiazoles and -benzoxazoles having antihistaminic and antiallergic activity.

The alkylaminobenzothiazoles and -benzoxazoles of the present invention surprisingly show a high degree of dopamine $D_4$ receptor binding affinity. Moreover, the present compounds have a selective affinity for the dopamine $D_4$ receptor over other dopamine receptors in the human body. The subject compounds also show variable affinity for other receptors such as, for example, serotonin receptors, histamine receptors, adrenergic receptors, cholinergic receptors and the σ-binding site.

The present invention concerns compounds having the formula

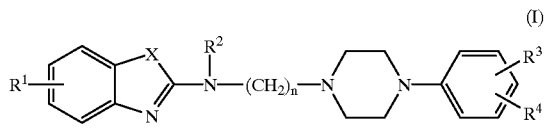

(I)

the N-oxide forms, the pharmaceutically acceptable acid addition salts and stereochemically isomeric forms thereof, wherein X is O or S;
n is 2, 3, 4 or 5;
$R^1$ is hydrogen, $C_{1-6}$alkyl, $C_{1-6}$alkyloxy or halo;
$R^2$ is hydrogen, $C_{1-6}$alkyl, phenyl, phenyl$C_{1-6}$alkyl or phenylcarbonyl;
$R^3$ and $R^4$ each independently are selected from hydrogen, halo, nitro, $C_{1-6}$alkyl, $C_{1-6}$alkyloxy, halo$C_{1-6}$alkyl, aminosulfonyl, mono- or di($C_{1-4}$alkyl)-aminosulfonyl; or $R^3$ and $R^4$ may also be taken together to form a bivalent radical of formula —CH=CH—CH=CH—.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-6}$alkyl is meant to include $C_{1-4}$alkyl and the higher homologues thereof having 5 or 6 carbon atoms such as, for example pentyl, 2-methylbutyl, hexyl, 2-methylpentyl and the like; halo$C_{1-6}$alkyl is defined as polyhalosubstituted $C_{1-6}$alkyl, in particular $C_{1-6}$alkyl substituted with 1 to 6 halogen atoms, more in particular difluoro- or trifluoromethyl.

The pharmaceutically acceptable acid addition salts as mentioned hereinabove are meant to comprise the therapeutically active non-toxic acid addition salt forms which the compounds of formula (I) are able to form. Said salts can be obtained by treating the base form of the compounds of formula (I) with appropriate acids such as inorganic acids, for example, hydrohalic acid, e.g. hydrochloric or hydrobromic, sulfuric, nitric, phosphoric and the like acids; or organic acids, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The term addition salt as used hereinabove also comprises the solvates which the compounds of formula (I) as well as the salts thereof, are able to form. Such solvates are for example hydrates, alcoholates and the like.

The N-oxides of the present compounds are meant to comprise those compounds of formula (I) wherein one or more nitrogen atoms are oxidized to the so-called N-oxide.

The term "stereochemically isomeric forms" as used hereinbefore and hereinafter defines all the possible isomeric forms in which the compounds of formula (I) may occur. Unless otherwise mentioned or indicated, the chemical designation of compounds denotes the mixture, and in particular the racemic mixture, of all possible stereochemically isomeric forms, said mixtures containing all diastereomers and enantiomers of the basic molecular structure. Stereochemically isomeric forms of the compounds of formula (I) and mixtures of such forms are obviously intended to be encompassed by formula (I).

Some of the compounds of formula (I) may also exist in their tautomeric form. Such forms although not explicitly indicated in the above formula are intended to be included within the scope of the present invention. For instance, compounds of formula (I) wherein $R^2$ is hydrogen may exist in their corresponding tautomeric form.

An interesting group of compounds are those compounds of formula (I) wherein X is S and $R^2$ is hydrogen, $C_{1-6}$alkyl, phenyl or phenyl$C_{1-6}$alkyl.

Another interesting group of compounds are those compounds of formula (I) wherein X is O and $R^2$ is hydrogen, $C_{1-6}$alkyl or phenyl$C_{1-6}$alkyl.

Also interesting compounds are those compounds of formula (I) wherein $R^3$ and $R^4$ are selected from the goup consisting of hydrogen, nitro, halo, $C_{1-6}$alkyl, $C_{1-6}$alkyloxy and trifluoromethyl, or $R^3$ and $R^4$ are taken together to form a bivalent radical of formula —CH=CH—CH=CH—.

Particular compounds are those interesting compounds wherein n is 2, 3 or 4.

Preferred compounds are those compounds of formula (I) wherein X is S, $R^2$ is hydrogen, $C_{1-6}$alkyl, phenyl or phenyl$C_{1-6}$alkyl, and n is 2.

Other preferred compounds are those compounds of formula (I) wherein $R^2$ and $R^3$ are hydrogen and $R^4$ is chloro.

Most preferred are the compounds
N-[2-[4-(3,4-dichlorophenyl)-1-piperazinyl]ethyl]-2-benzothiazolamine;
N-[2-(4-phenyl-1-piperazinyl)ethyl]-2-benzothiazolamine;
N-[2-[4-(4-chlorophenyl)-1-piperazinyl]ethyl]-2-benzothiazolamine;
N-[2-[4-(4-bromophenyl)-1-piperazinyl]ethyl]-2-benzothiazolamine; the N-oxides, the stereoisomeric forms and the pharmaceutically acceptable acid addition salts thereof.

The compounds of the present invention can generally be prepared by N-alkylating an intermediate of formula (III) with an intermediate of formula (II) wherein $W^1$ represents an appropriate reactive leaving group such as, for example, a halogen.

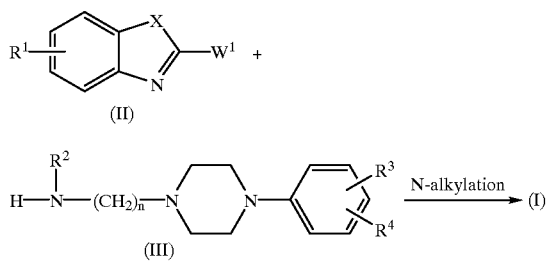

Said N-alkylation may be performed by stirring and heating the reactants in a reaction-inert solvent such as ethanol, 2-ethoxyethanol, 1-butanol, methylisobutylketon or toluene, preferably in the presence of a suitable base such as sodiumcarbonate, and optionally in the presence of a catalyst such as, for example, potassium iodide.

In this and the following preparations, the reaction products may be isolated from the reaction medium and, if necessary, further purified according to methodologies generally known in the art such as, for example, extraction, crystallization, trituration and chromatography.

Compounds of formula (I) wherein X is S, said compounds being represented by formula (I-a), may be prepared by reacting an intermediate of formula (III) with an intermediate of formula (IV) in a reaction-inert solvent such as, for example, tetra-hydrofuran, and subsequently cyclizing the thus formed intermediate of formula (V) in a reaction-inert solvent such as, for example, chloroform, and in the presence of a suitable reagent such as, for example, thionylchloride. Alternatively, compounds of formula (I-a) can be prepared by directly mixing an intermediate of formula (III) with an intermediate of formula (IV) in a reaction-inert solvent, such as, for example, chloroform, in the presence of a suitable reagent such as, for example, thionylchloride, thus forming in situ an intermediate of formula (V) which is immediately cyclized during the course of the reaction.

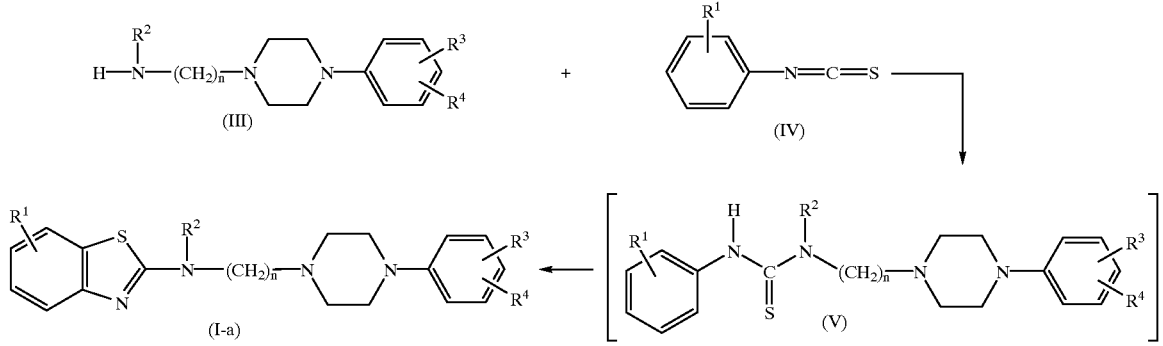

The present compounds can also be prepared by N-alkylating an intermediate of formula (VI) with an intermediate of formula (VII) wherein $W^2$ is an appropriate leaving group such as, for example, a halogen, optionally in a reaction inert solvent such as, for example, dimethylacetamide.

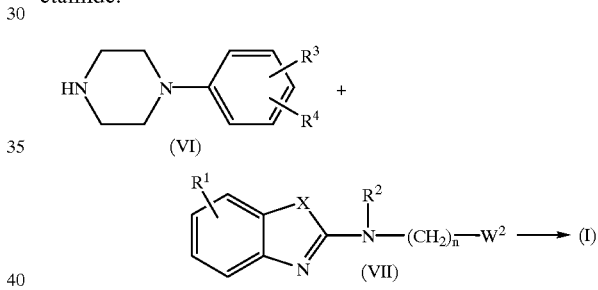

Alternatively, the compounds of formula (I) can be prepared by N-alkylating an intermediate of formula (XV) with an intermediate of formula (XVI) wherein $W^2$ is an appropriate leaving group such as, for example, a halogen, in a reaction-inert solvent such as, for example, tetrahydrofuran, and, in the presence of a suitable base such as, for example, sodium hydride or a functional equivalent thereof.

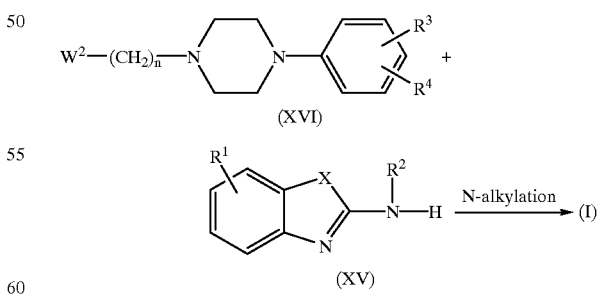

The compounds of formula (I) may be also converted into other compounds of formula (I) following art-known transformation reactions. For instance, compounds of formula (I) wherein $R^2$ is hydrogen, said compounds being represented by formula (I-b), may be converted into compounds of formula (I) wherein $R^2$ is other than hydrogen.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Intermediates and starting materials used in the above reaction procedures are mostly known compounds which are commercially available or may be prepared according to art-known procedures. For instance, intermediates of formula (XV) may be prepared according to the procedure described in J. Chem. Soc., 1962, 230, and intermediates of formula (XVI) may be prepared according to the procedure as described in JP 60202883.

The intermediates of formula (III) can generally be prepared by hydrolysis of a carbamate ester of formula (VIII) in a reaction-inert solvent such as, for example, isopropanol and in the presence of a suitable base such as, for example, potassium hydroxide. It may further be convenient to perform said reaction at reflux temperature.

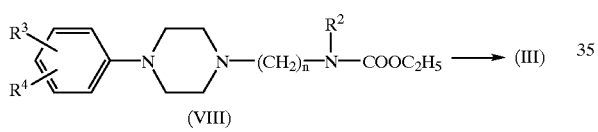

Intermediates of formula (VIII) may be prepared by N-alkylating a piperazine derivative of formula (IX) with a carbamate ester of formula (X) wherein $W^3$ is an appropriate leaving group such as, for example, a halogen.

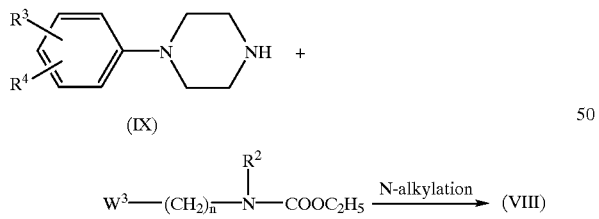

Said reaction may be performed by stirring and heating the reactants in a reaction-inert solvent such as, for example, 4-methyl-2-pentanone, in the presence of a suitable base such as sodiumcarbonate, and optionally in the presence of a catalytic amount of a potassium salt such as, for example, potassium iodide.

Intermediates of formula (III) wherein $R^2$ is hydrogen, said intermediates being represented by formula (III-a), can also be prepared by catalytic hydrogenation of a nitrile derivative of formula (XI) using hydrogen in the presence of an appropriate catalyst such as, for example, Raney-nickel.

It may be convenient to perform said reaction in a reaction-inert solvent such as, for example, tetrahydrofuran or methanol saturated with $NH_3$.

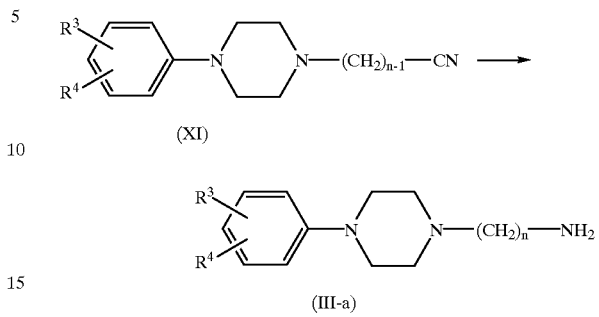

Intermediates of formula (XI) may be prepared by N-alkylating a piperazine derivative of formula (IX) with a nitrile derivative of formula (XII) wherein $W^4$ is an appropriate leaving group such as, for example, a halogen, in an analogous way as intermediates (VIII) were prepared starting form intermediates (IX) and (X).

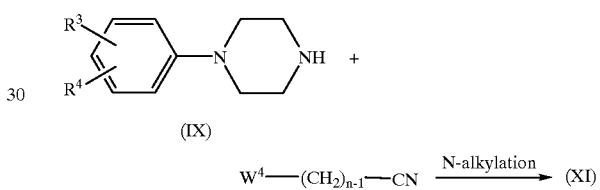

Alternatively, nitrile derivatives of formula (XI) wherein (n-1) is 2, said derivatives being represented by formula (XI-a), may be prepared by N-alkylating a piperazine derivative of formula (IX) with acrylonitrile by stirring and heating the reactants in a reaction-inert solvent such as, for example, 2-propanol, and optionally in the presence of a catalytic amount of a quaternary ammonium salt such as, for example, N-methyl-N,N-dioctyl octanaminiumchloride.

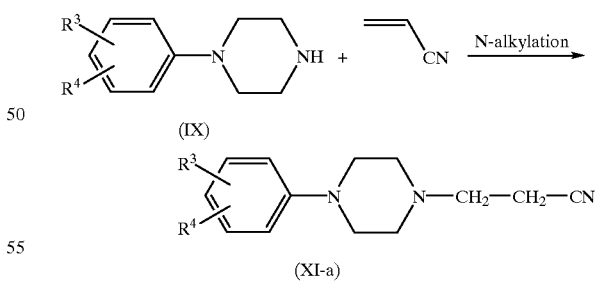

Intermediates of formula (VII) may be prepared by first N-alkylating an intermediate of formula (XIII) with an intermediate of formula (II) and subsequently replacing the hydroxy group of the thus obtained intermediate of formula (XIV) by a suitable leaving group $W^4$, such as, for example, chloro. For instance, intermediates of formula (XIV) may be reacted with thionylchloride to form an intermediate of formula (VII) wherein $W^4$ is chloro.

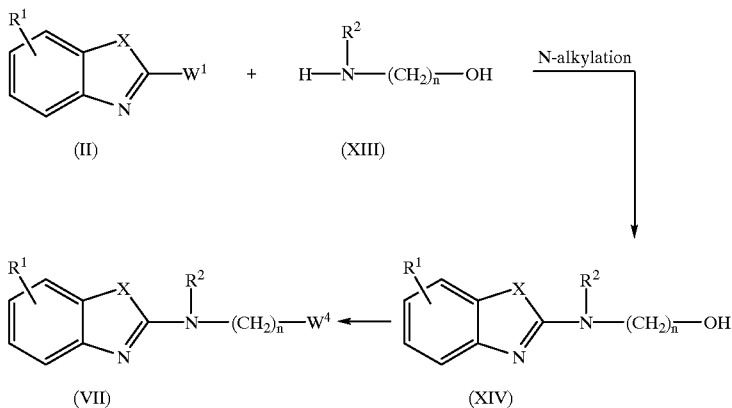

An alternative way to prepare intermediates of formula (VII) includes the N-alkylation of an intermediate of formula (XV) with an intermediate of formula (XVII) wherein LG is a leaving group such as bromo and $W^2$ is a leaving group as defined in intermediates of formula (VII) whereby LG is chosen as such that the substitution reaction with the intermediate of formula (XV) will preferentially occur on the carbon atom bearing the LG moiety. Said reaction is preferably performed in a reaction-inert solvent in the presence of a suitable base such as, for example, sodium hydride.

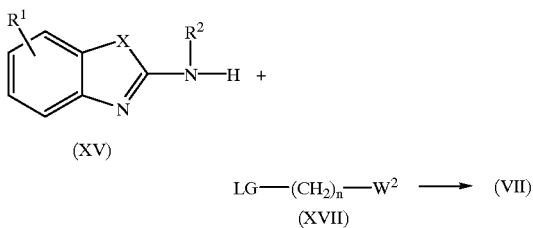

In a similar way, intermediates of formula (XVI) may be prepared by N-alkylating an intermediate of formula (IX) with an intermediate of formula (XVII).

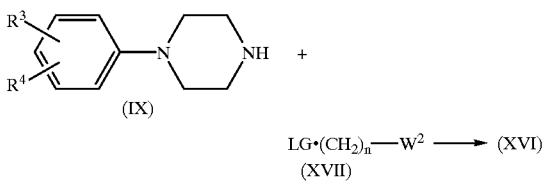

Some of the compounds of formula (I) and some of the intermediates in the present invention contain at least one asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

An alternative manner of separating the enantiomeric forms of the compounds of formula (I) and intermediates involves liquid chromatography, in particular liquid chromatography using a chiral stationary phase.

Pure stereochemically isomeric forms of the compounds of formula (I) may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), the N-oxides, the pharmaceutically acceptable acid addition salts and stereochemically isomeric forms thereof, are potent antagonists of the dopamine $D_4$ receptor, i.e. they show a high degree of dopamine $D_4$ receptor binding affinity thus inhibiting the binding of an endogeneous ligand, in particular dopamine, to the dopamine $D_4$ receptor, as is demonstrated in the pharmacological example described hereinafter. The antagonistic effect of the binding of the present compounds to the dopamine $D_4$ receptor was confirmed in signal-transduction assays.

The present compounds show interesting activity in the so-called "differential reinforcement test low rate 72 seconds"-test (DRL-72) which is an in vivo test where most clinically active antidepressants given at high doses show activity. In said test, rats can obtain food by pressing a lever only when they have waited a full 72 seconds between two lever presses. The present $D_4$ antagonists induce a more efficient behaviour of the rats whereas untreated animals find it difficult to control their impulsive tendency to press the lever and to subordinate it to appropriate timing so as to maximize their award. The usefulness of this DRL-72 test as a model for specific $D_4$ antagonists such as the present compounds is further supported by the fact that (a) Manki et al. (Journal of Affective Disorders 40 (1996), 7–13) found that there is a significant association between the $D_4$ receptor gene polymorphism and mood disorders, and (b) by the fact that $D_4$ receptors are known to be most dense in hippocampus, entorhinal and cerebral cortex in the primates, humans as well as rodents.

Antagonizing the dopamine $D_4$ receptor will suppress or relieve a variety of symptoms associated with phenomena induced by the activation, in particular the excessive activation, of said receptor. Consequently, the ability of the present compounds to alter dopamine $D_4$ mediated neurotransmission makes them of potential use in the treatment and/or prevention of a variety of disorders associated therewith such as sleep disorders, sexual disorders, thought disorders, impaired information processing, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, gastrointestinal disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol dependencies, vascular and cardiovascular disorders, ocular disorders, dystonia, tardive dyskinesia, Gilles De la Tourette's syndrome and other hyperkinesias, dementia, ischemia, movement disorders such as akathesia, hypertension and diseases caused by a hyperactive immune system such as allergies and inflammation.

The compounds of the present invention distinctively show affinity for the dopamine $D_4$ receptor in comparison with other dopamine receptors such as, for example, the dopamine $D_2$ receptor. Such a dissociation between dopamine $D_4$ receptor antagonizing activity and other dopamine receptor activity may be of additional use in the treatment and/or prevention of the above-mentioned disorders. For example, Van Tol et al. (Nature 1991, 350, 610–614) suggested that compounds which can interact selectively with the dopamine $D_4$ receptor, whilst having a less pronounced action at the dopamine $D_2$ receptor, might have the same beneficial level of antipsychotic activity as classical antipsychotics with the additional benefit of being less prone to the undesired extrapyramidal or neuroendocrine side-effects of classical antipsychotics. It is therefore that the present compounds are particularly useful as antipsychotics, especially in the treatment and/or prevention of psychotic disorders such as schizophrenia.

In addition to their potency to antagonize the dopamine $D_4$ receptor, the subject compounds also show variable affinity for other receptors such as, for example, serotonin receptors, histamine receptors, adrenergic receptors, cholinergic receptors and the σ-binding site. For instance, some of the present compounds show a favourable binding affinity for the σ-binding site, the 5 $HT_{1A}$ receptor and the $\alpha_2$-receptor.

In view of the usefulness of the subject compounds in the treatment and/or prevention of disorders associated with the excessive activation of the dopamine $D_4$ receptor, in particular in the treatment of psychotic disorders such as schizophrenia, the present invention provides a method of treating warm-blooded animals suffering from such disorders, said method comprising the systemic administration of a dopamine $D_4$ receptor antagonizing amount of a compound of formula (I), a N-oxide, a stereo-chemically isomeric form or a pharmaceutically acceptable acid addition salt thereof.

The present invention thus also relates to compounds of formula (I) as defined hereinabove for use as a medicine. Further, the present invention also relates to the use of a compound of formula (I) for the manufacture of a medicament for treating psychotic disorders.

Another aspect of the present invention involves the ability of the present compounds to act as lipid lowering agents. Some of the present compounds of formula (I) were tested in animals and showed a marked lipid lowering effect rendering the present compounds useful agents in the treatment or prophylaxis of hyperlipidemia or atherosclerosis.

The term "dopamine $D_4$ receptor antagonizing amount", as used herein, refers to an amount sufficient to inhibit the binding of an endogeneous ligand, in particular dopamine, to the dopamine $D_4$ receptor. Those of skill in the treatment of the disorders as mentioned hereinabove could determine that an effective dopamine $D_4$ receptor antagonizing daily amount would be from about 0.01 mg/kg to about 10 mg/kg body weight, more preferably from about 0.04 mg/kg to about 4 mg/kg body weight. The compounds may be administered on a regimen of 1 to 4 times per day.

In order to alleviate the symptoms of psychotic disorders such as schizophrenia without causing undesired side-effects, the dosage level of the compound according to the invention is ideally selected such that the dose administered is effective in substantially completely blocking the dopamine $D_4$ receptor while displaying a favourable dopamine $D_2$ receptor occupancy causing no or negligible undesired extrapyramidal or neuroendocrine side-effects.

If desired, the compounds according to this invention may be co-administered with another antipsychotic, for example one producing its effects via one or more of the following mechanisms: dopamine $D_2$ receptor blockade, 5-$HT_2$ receptor blockade, 5-$HT_{1A}$ agonism and 5-$HT_3$ antagonism. In such circumstances, an enhanced antipsychotic effect may be envisaged without a corresponding increase in side-effects such as those caused by, for example, strong dopamine $D_2$ receptor blockade; or a comparable antipsychotic effect with reduced side-effects may alternatively be envisaged. Such co-administration may be desirable where a patient is already established on a, for example, anti-schizophrenic treatment regime involving conventional anti-schizophrenic medicaments.

For administration purposes, the subject compounds may be formulated into various pharmaceutical forms. To prepare the pharmaceutical compositions of this invention, an effective dopamine $D_4$ receptor antagonizing amount of the particular compound, as acid addition salt or in its free base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid addition salts of the compounds of formula (I) due to their increased water solubility over the corresponding free base form, are more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Due to their high degree of specificity to the dopamine $D_4$ receptor, the compounds of formula (I) as defined above, are also useful to mark or identify receptors, in particular dopamine $D_4$ receptors. To this purpose, the compounds of the present invention need to be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}C$-atom or tritium atom.

One particular group consists of those compounds of formula (I) wherein $R^1$ and/or $R^3$ and/or $R^4$ are a radioactive halogen atom. In principle, any compound of formula (I) containing a halogen atom is prone for radiolabelling by replacing the halogen atom by a suitable isotope. Suitable halogen radioisotopes to this purpose are radioactive iodides, e.g. $^{122}I$, $^{123}I$, $^{125}I$, 131I; radioactive bromides, e.g. $^{75}Br$, $^{76}Br$, $^{77}Br$ and $^{82}Br$, and radioactive fluorides, e.g. $^{18}F$. The introduction of a radioactive halogen atom can be performed by a suitable exchange reaction or by using any one of the procedures as described hereinabove to prepare halogen derivatives of formula (I).

Preferred labelled compounds are those compounds of formula (I), wherein $R^1$ and/or $R^3$ and/or $R^4$ are $^{123}I$, $^{125}I$, $^{75}Br$, $^{76}Br$, $^{77}Br$ or $^{18}F$.

Another interesting form of radiolabelling is by substituting a carbon atom by a $^{11}C$-atom or the substitution of a hydrogen atom by a tritium atom. For instance, introducing such a $^{11}C$-atom may be carried out by N-alkylating a compound of formula (I), wherein $R^2$ is hydrogen using a $^{11}C$-labelled alkylating reagent.

Hence, said radiolabelled compounds of formula (I) can be used in a process of specifically marking dopamine $D_4$ receptor sites in biological material. Said process comprises the steps of (a) radiolabelling a compound of formula (I), (b) administering this radiolabelled compound to biological material and subsequently (c) detecting the emissions from the radiolabelled compound. The term biological material is meant to comprise every kind of material which has a biological origin. More in particular this term refers to tissue samples, plasma or body fluids but also to animals, specially warm-blooded animals, or parts of animals such as organs. The radiolabelled compounds of formula (I) are also useful as agents for screening whether a test compound has the ability to occupy or bind to a dopamine $D_4$ receptor site. The degree to which a test compound will displace a compound of formula (I) from the dopamine $D_4$ receptor site will show the test compound ability as either an agonist, an antagonist or a mixed agonist/antagonist of a dopamine $D_4$ receptor. When used in in vivo assays, the radiolabelled compounds are administered in an appropriate composition to an animal and the location of said radiolabelled compounds is detected using imaging techniques, such as, for instance. Single Photon Emission Computerized Tomography (SPECT) or Positron Emission Tomography (PET) and the like. In this manner the distribution of dopamine $D_4$ receptor sites throughout the body can be detected and organs containing dopamine $D_4$ receptor sites such as, for example, the brain, can be visualized by the imaging techniques mentioned hereinabove. This process of imaging an organ by administering a radiolabelled compound of formula (I), which binds to the dopamine $D_4$ receptor sites and detecting the emissions from the radioactive compound also constitutes a part of the present invention.

The following examples are intended to illustrate and not to limit the scope of the present invention.

Experimental Part

A. Preparation of the Intermediate Compounds

EXAMPLE A.1 a) A mixture of 1-(4-bromophenyl)piperazine (0.018 mol) and ethyl (2-chloroethyl)-carbamate (0.036 mol) was stirred for 2 hours at 130° C. Triethylamine (3 ml) was added and the mixture was stirred for 15 minutes at 130° C. The reaction mixture was cooled to room temperature, $CH_2Cl_2$ was added and the resulting mixture was washed with water. The organic layer was separated, dried, filtered and the solvent was evaporated. The residue was purified by column chromatography over silica gel (eluent: $CH_2Cl_2/CH_3OH$ 95/5). The pure fractions were collected and the solvent was evaporated, yielding 4.3 g (67.2%) of ethyl [2-[4-(4-bromophenyl)-1-piperazinyl]-ethyl]carbamate (interm. 1).

b) A mixture of intermediate (1) (0.029 mol) and potassium hydroxide (0.29 mol) in 2-propanol (200 ml) was stirred and refluxed for 8 hours. $CH_2Cl_2$ was added. Water was added dropwise to dissolve the potassium-salts. The organic layer was separated, dried, filtered and the solvent was evaporated. The residue was purified by column chromatography over silica gel (eluent: $CH_2Cl_2/(CH_3OH/NH_3)$ 90/10). The pure fractions were collected and the solvent was evaporated, yielding 3.8 g (46%) of 4-(4-bromophenyl)-1-piperazineethanamine (interm. 4).

In a similar way were prepared
4-(4-iodophenyl)-1-piperazineethanamine (interm. 11);
4-(1-naphtalenyl)-1-piperazinepentanamine (interm. 12);
4-(1-naphtalenyl)-1-piperazineethanamine (interm. 13);
4-(1-naphtalenyl)-1-piperazinepropanamine (interm. 14);
4-(4-nitrophenyl)-1-piperazinepropanamine (interm. 15);
4-(4-bromophenyl)-1-piperazinebutanamine (interm. 16); and
4-(4-bromophenyl)-1-piperazinepropanamine (interm. 17).

EXAMPLE A.2 a) A mixture of 1-(3,4-dichlorophenyl)piperazine (0.1 mol), 5-chloropentanenitrile (0.13 mol), sodium carbonate (10 g) and potassium iodide (0.1 g) in 4-methyl-2-pentanone (280 ml) was stirred and refluxed for 10 hours. The reaction mixture was cooled, filtered and the filtrate was evaporated. The residue was purified by column chromatography over silica gel (eluent: $CH_2Cl_2/CH_3OH$ 95/5). The pure fractions were collected and the solvent was evaporated, yielding 22.5 g (72%) of 4-(3,4-dichlorophenyl)-1-piperazinepentanenitrile (interm. 2).

b) A mixture of intermediate (2) (0.072 mol) in tetrahydrofuran (250 ml) was hydrogenated with Raney nickel (2 g) as a catalyst. After uptake of $H_2$, the catalyst was filtered off and the filtrate was evaporated. The residue was stirred in diisopropylether, filtered off over dicalite and the filtrate was evaporated, yielding 20 g (88%) of 4-(3,4-dichlorophenyl)-1-piperazinepentanamine (interm. 5).

In a similar way were prepared:
4-(2,4-dimethylphenyl)-1-piperazineethanamine(interm. 18);
4-(2,4-dimethylphenyl)-1-piperazinebutanamine (interm. 19);
4-(2,4-dimethylphenyl)-1-piperazinepentanamine (interm. 20);
4-(3,4-dichlorophenyl)-1-piperazinepropanamine (interm. 21);
4-(3,4-dichlorophenyl)-1-piperazinebutanamine (interm. 22); and
4-phenyl-1-piperazinepropanamine (interm. 23).

EXAMPLE A.3

A mixture of 1-(3,4-dichlorophenyl)piperazine (0.1 mol), 2-propenenitrile (0.15 mol), and N-methyl-N,N-dioctyl octanaminiumchloride (1 ml) in 2-propanol (150 ml) was stirred and refluxed for one hour. The solvent was evaporated and the residue was purified by column chromatography over silica gel (eluent: $CH_2Cl_2/CH_3OH$ 95/5). The pure fractions were collected and the solvent was evaporated. The residue was stirred in diisopropylether/acetonitrile 10/1. The solvent was evaporated, yielding 28 g (98.5%) of 4-(3,4-dichlorophenyl)-1-piperazinepropanenitrile (interm. 3).

EXAMPLE A.4

A mixture of 4-(3,4-dichlorophenyl)-1-piperazineethanamine (0.01 mol) and 4-methyl-1-isothiocyanatobenzene (0.01 mol) in tetrahydrofuran (300 ml) was stirred at room temperature for 1 hour. The solvent was evaporated. The residue was recrystallized from DIPE. The precipitate was filtered off and dried. The product was used without further purification, yielding 4.2 g N-(4-methylphenyl)-N'-[2-[4-(3,4-dichlorophenyl)-1-piperazinyl]ethyl]thiourea (interm. 6).

EXAMPLE A.5 a) A mixture of 5-(methylamino)pentanol (0.23 mol), 2-chlorobenzothiazole (0.3 mol), sodium carbonate (0.4 g) and potssium iodide (catalytic quantity) in methylisobutylketon (1000 ml) was stirred and refluxed overnight. The reaction mixture was cooled, washed with water, dried, filtered and the filtrate was evaporated. The residue was stirred in water, acidified with HCl, stirred, washed with diisopropylether, and the acidic layer was alkalized with $NH_4OH$. This mixture was extracted twice with $CH_2Cl_2$. The separated organic layer was dried, filtered, and the solvent was evaporated, yielding 56 g of N-(5-hydroxypentyl)-N-methyl-2-benzothiazolamine (interm. 7).

b) Thionylchloride (60 ml) was stirred in $CHCl_3$ (400 ml). A solution of intermediate (7) (0.22 mol) in $CHCl_3$ (200 ml) was added dropwise. The mixture was stirred at room temperature overnight. The solvent was evaporated and the residue was dissolved in $CH_2Cl_2$, washed with water, dried, filtered and the solvent was evaporated, yielding 65 g of N-(5-chloropentyl)-N-methyl-2-benzothiazolamine (interm. 8).

EXAMPLE A.6

A mixture of 1-(3,4-dichlorophenyl)-piperazine (0.05 mol), 1-bromo-2-chloroethane (0.1 mol) and triethylamine (0.05 mol) was stirred for 30 minutes at 100° C. The mixture was cooled, then partitioned between $CH_2Cl_2$ and water. The layers were separated. The organic phase was filtered over dicalite. The organic filtrate was dried, filtered and the filtrate was evaporated. The residue was purified by column chromatography over silica gel (eluent: $CH_2Cl_2/CH_3OH$ 98/2). The pure fractions were collected and the solvent was evaporated, yielding 5.2 g (35%) of 4-(2-chloroethyl)-1-(3, 4-dichlorophenyl)-piperazine (interm. 9).

EXAMPLE A.7

Sodium hydride (0.05 mol) was added portionwise to a solution of N-phenyl-2-benzothiazolamine, prepared according to the procedure described in J. Chem. Soc, 1962, 230, (0.05 mol) in tetrahydrofuran (200 ml). The mixture was stirred for 15 minutes. A solution of 1-bromo-4-chlorobutane (0.05 mol) in tetrahydrofuran (50 ml) was added dropwise and the resulting reaction mixture was stirred and refluxed for 48 hours. The mixture was cooled, and the solvent was evaporated. The residue was partitioned between water and $CH_2Cl_2$. The organic layer was separated, dried, filtered and the solvent evaporated. The residue was purified by column chromatography over silica gel (eluent: $CH_2Cl_2$). The desired fractions were collected and the solvent was evaporated, yielding 10.4 g (66%) of N-(4-chlorobutyl)-N-phenyl-2-benzothiazolamine (interm. 10).

N-(5-chloropentyl)-N-phenyl-2-benzothiazolamine (interm. 24) was prepared similarly.

B. Preparation of the Final Compounds

EXAMPLE B.1 a) A mixture of intermediate (5) (0.015 mol), 2-chlorobenzthiazole (0.016 mol) and sodium carbonate (4 g) in toluene (150 ml) was stirred and refluxed overnight. The reaction mixture was cooled and filtered. The filtrate was evaporated and the residue was purified by column chromatography over silica gel (eluent: $CH_2Cl_2/CH_3OH$ 95/5). The desired fractions were collected, the solvent was evaporated and the residue was crystallized from $CH_3CN$. The precipitate was filtered off and dried, yielding 2.3 g (34%) of N-[5-[4-(3,4-dichlorophenyl)-1-piperazinyl]pentyl]-2-benzothiazolamine (comp. 1).

b) N-[3-[4-phenyl-1-piperazinyl]propyl]-2-benzothiazolamine (comp. 5) was prepared according to the same procedure as described in example B.1.a) but using ethanol instead of toluene.

c) N-[4-[4-(4-methoxyphenyl)-1-piperazinyl]butyl]-2-benzothiazolamine (comp. 26) was prepared according to the same procedure as described in example B.1.a) but using methylisobutylketon instead of toluene.

d) N-[3-[4-[3-(trifluoromethyl)phenyl]-1-piperazinyl]propyl]-2-benzothiazolamine (comp. 27) was prepared according to the same procedure as described in example B.1.a) but using 2-ethoxyethanol instead of toluene.

e) N-[4-[4-(3,4-dichlorophenyl)-1-piperazinyl]butyl]-6-methyl-2-benzothiazolamine (comp. 52) was prepared according to the same procedure as described in example B.1.d) but a catalytic amount of potassium iodide was added to the starting reaction mixture.

EXAMPLE B.2

4-(3,4-dichlorophenyl)-1-piperazinebutanamine (0.0085 mol), prepared according to the procedure described in example A.5, and 2-chloro-6-methoxybenzothiazole (0.0043 mol) was stirred at 120° C. for 1 hour. The mixture was cooled to room temperature, diluted with $CH_2Cl_2$ and converted into the free base with $NH_4OH$. The organic layer was separated, dried ($MgSO_4$), filtered and the solvent was evaporated. The residue was purified by column chromatography over silica gel (eluent: $CH_2Cl_2/CH_3OH$ 90/10). The pure fractions were collected and the solvent was evaporated. The residue was converted into the (E)-2-butenedioic acid salt (1:1). The precipitate was filtered off and dried, yielding 1.1 g (44%) of N-[4-[4-(3,4-dichlorophenyl)-1-piperazinyl]butyl]-6-methoxy-2-benzothiazolamine (E)-2-butenedioate(1:1) (comp. 42).

EXAMPLE B.3

Intermediate (6) (0.01 mol) was dissolved in $CHCl_3$ (30 ml). The mixture was cooled to 0° C. Thionyl chloride (11.5 ml) was added dropwise slowly. The mixture was allowed to warm slowly to room temperature and then stirred for 30 minutes. The solvent was evaporated and the residue was washed with a small amount of HCl/2-propanol in 2-propanone, filtered, washed with 2-propanone and converted into the free base with a $NH_4OH$ solution. The precipitate was filtered off and purified by column chromatography over silica gel (eluent: $CH_2Cl_2/CH_3OH$ 95/5). The pure fractions were collected and the solvent was evaporated, yielding: 0.7 g (16.7%) of N-[2-[4-(3,4-dichlorophenyl)-1-piperazinyl]ethyl]-6-methyl-2-benzothiazolamine (comp. 53).

EXAMPLE B.4

A mixture of 4-(3,4-dichlorophenyl)-1-piperazinepropanamine (0.009 mol), prepared according to the procedure described in Example A.5, and 1-isothiocyanato-4-methoxybenzene (0.009 mol) in $CHCl_3$ (100 ml) was stirred for one hour at room temperature, then cooled to 0° C. on an ice-bath. Thionylchloride (30 ml) was added dropwise and the resulting reaction mixture was allowed to slowly warm to room temperature. The reaction mixture was stirred for 3 hours at 60° C. The mixture was cooled to room temperature and the resulting precipitate was filtered off, stirred in boiling 2-propanone, filtered off, then dried. This fraction was converted into the free base by addition of aqueous ammonia. The mixture was extracted with $CH_2Cl_2$. The separated organic layer was dried, filtered and the solvent evaporated. The residue was crystallized from $CH_3CN$, filtered off, dissolved in 2-propanone and converted into the hydrochloric acid salt (1:2) with HCl/2-propanol. The precipitate was filtered off and dried, yielding 1.6 g (34%) of N-[3-[4-(3,4-dichlorophenyl)-1-piperazinyl]propyl]-6-methoxy-2-benzothiazolamine dihydrochloride (comp. 72).

EXAMPLE B.5

A mixture of compound (1) (0.01 mol), chloromethylbenzene (5 ml) and sodium hydride (0.015 mol; 60% solution) in tetrahydrofuran (200 ml) was stirred and refluxed for 8 hours. The reaction mixture was cooled and a few drops of water were added. The solvent was evaporated. The residue was partitioned between water and $CH_2Cl_2$. The organic layer was separated, washed with water, dried, filtered and the solvent was evaporated. The residue was purified by column chromatography over silica gel (eluent: $CH_2Cl_2/$ ethylacetate 70/30). The pure fractions were collected and the solvent was evaporated. The residue was dissolved in 2-propanol and converted into the (E)-2-butenedioic acid salt (1:1) with (E)-2-butenedioic acid (1 g). The mixture was boiled, then stirred overnight at room temperature. The precipitate was filtered off and dried, yielding 2.70 g (41%) of N-[5-[4-(3,4-dichlorophenyl)-1-piperazinyl]pentyl]-N-phenylmethyl-2-benzothiazolamine (E)-2-butenedioate(1:1) (comp. 112).

EXAMPLE B.6

A mixture of compound (3) (0.01 mol), sodium carbonate (4 g) and benzoylchloride (0.01 mol) in chloroform (150 ml) and N,N-dimethylformamide (1 drop) was stirred and refluxed for 4 hours. The mixture was filtered warm and the filtrate was washed with water. The organic layer was separated, dried, filtered and the solvent was evaporated. The residue was purified over silica gel on a glass filter (eluent: $CH_2Cl_2$/ethanol 95/5). The pure fractions were collected and the solvent was evaporated. The residue was crystallized from $CH_3CN$. The precipitate was filtered off and dried, yielding 4.8 g (92.5%) of N-(2-benzothiazolyl)-N-[3-[4-(3,4-dichlorophenyl)-1-piperazinyl]propyl] benzamide (comp. 99).

EXAMPLE B.7

A mixture of 1-(3,4-dichlorophenyl)piperazine (0.03 mol) and intermediate (8) (0.02 mol) in dimethylacetamide (2 ml) was stirred for 2 hours at 120–130° C. The reaction mixture was cooled, dissolved in $CH_2C_2$, washed with aqueous ammonia, dried, filtered, and the filtrate was evaporated. The residue was purified by column chromatography over silica gel (eluent: $CH_2Cl_2/CH_3OH$ 98/2), then repurified (eluent: $CH_2Cl_2$/ethylacetate 50/50). The pure fractions were collected and the solvent was evaporated. The residue was dissolved in 2-propanol and converted into the (E)-2-butenedioic acid salt (1:1) with (E)-2-butenedioic acid (2 g). The mixture was boiled, then stirred at room temperature. The precipitate was filtered off and dried, yielding 6.60 g (57%) of N-[5-[4-(3,4-dichlorophenyl)-1-piperazinyl]pentyl]-2-benzothiazolamine (E)-2-butenedioate(1:1) (comp. 110).

EXAMPLE B.8

Compound 12 (0.0058 mol) was dissolved in warm ethanol (75 ml). (E)-2-Butenedioic acid (0.0058 mol) was added and the resulting mixture was stirred until complete dissolution. The mixture was allowed to cool to room temperature with stirring. The precipitate was filtered off and dried, yielding 2.03 g (80%) of N-[2-[4-(4-chlorophenyl)-1-piperazinyl]ethyl]-2-benzothiazolamine. (E)-2-butenedioate (2:1) (comp. 127).

EXAMPLE B.9

Compound 2 (0.015 mol) was dissolved in tetrahydrofuran (200 ml). Sodium hydride (0.02 mol) was added. The mixture was stirred for 15 minutes at room temperature. Dimethyl sulphate (0.015 mol) was added and the resulting reaction mixture was stirred for 4 hours at room temperature. The solvent was evaporated and the residue was purified over silica gel (eluent: ethylacetate/CH$_3$OH/CH$_2$Cl$_2$ 30/0/70, upgrading to 28/2/70). The pure fractions were collected and the solvent was evaporated. The residue was dissolved in 2-propanol and converted into the (E)-2-butenedioic acid salt (1:1) with (E)-2-butenedioic acid (0.8 g). The mixture was boiled, then stirred overnight at room temperature. The precipitate was filtered off and dried, yielding 1.80 g (23%) of N-[2-[4-(3,4-dichlorophenyl)-1-piperazinyl]ethyl ]-N-methyl-2-benzothiazolamine (E)-2-butenedioate(1:1) (comp. 117).

EXAMPLE B.10

A mixture of 4-(4-chlorophenyl)-1-piperazineethanamine (0.01 mol) and 1-isothiocyanato-2-methoxybenzene (0.01 mol) in CCl$_4$ (100 ml) was stirred for 1 hour at room temperature. Br$_2$ in CCl4 (0.01 mol in 10 ml) was added and the reaction mixture was stirred and refluxed for 1 hour. The reaction mixture was cooled to room temperature, diluted with CH$_2$Cl$_2$, and aqueous NH$_3$ was added. The organic layer was dried, filtered, and the solvent was evaporated. The residue was purified by column chromatography over silica gel (eluent: CH$_2$Cl$_2$/CH$_3$OH 95/5). The pure fractions were collected and the solvent was evaporated. The residue was converted into the hydrochloric acid salt (1:2). The precipitate was filtered off and dried, yielding 0.4 g (8%) of N-[2-[4-(4-chlorophenyl)-1-piperazinyl]ethyl]-7-methoxy-2-benzothiazolamine hydrochloride (1:2) hydrate (1:1) (comp. 143).

EXAMPLE B.11

N-[2-[4-(4-chlorophenyl)-1-piperazinyl]ethyl]-6-fluoro-2-benzothiazolamine (comp 141) was prepared according to the procedure described in example B.10 but using SOCl$_2$ in CHCl$_3$ instead of Br$_2$ in CCl$_4$.

EXAMPLE B.12

N-phenyl-2-benzothiazolamine, prepared according to the procedure described in J. Chem. Soc, 1962, 230, (0.03 mol) was dissolved in tetrahydrofuran (100 ml). Sodium hydride (0.03 mol) was added portionwise. The mixture was stirred for 15 minutes. A solution of intermediate 9 (0.018 mol) in tetrahydrofuran (50 ml) was added. The resulting reaction mixture was stirred and refluxed overnight. The reaction mixture was cooled and the solvent was evaporated. The residue was dissolved in CH$_2$Cl$_2$. The organic solution was washed with water, dried, filtered, and the solvent was evaporated. The residue was purified by column chromatography over silica gel (eluent: CH$_2$Cl$_2$/ethylacetate 90/10). The desired fractions were collected and the solvent was evaporated. The residue was dissolved in 2-propanol and converted into the (E)-2-butenedioic acid salt (1:1) with (E)-2-butenedioic acid (1.5 g). The mixture was boiled, then allowed to cool to room temperature. The precipitate was filtered off and dried, yielding 3.66 g (94%) of N-[2-[4-(3,4-dichlorophenyl)-1-piperazinyl]ethyl]-N-phenyl-2-benzothiazolamine (E)-2-butenedioate (1:1) (comp. 114).

The following compounds were prepared according to one of the above examples.

TABLE 1

| Comp. No. | Ex. No. | n | R$^1$ | R$^3$ | R$^4$ | Physical data |
|---|---|---|---|---|---|---|
| 1 | B.1.a | 5 | H | 3-Cl | 4-Cl | mp. 128.8° C. |
| 2 | B.1.a | 2 | H | 3-Cl | 4-Cl | mp. 159.6° C. |
| 3 | B.1.a | 3 | H | 3-Cl | 4-Cl | mp. 139.1° C. |
| 4 | B.1.a | 4 | H | 3-Cl | 4-Cl | mp. 156.2° C. |
| 5 | B.1.b | 3 | H | H | H | — |
| 6 | B.1.b | 2 | H | H | H | — |
| 7 | B.1.b | 3 | H | 3-Cl | H | — |
| 8 | B.1.b | 4 | H | H | H | — |
| 9 | B.1.b | 4 | H | 3-Cl | H | — |
| 10 | B.1.b | 3 | H | 4-Cl | H | — |
| 11 | B.1.b | 4 | H | 4-Cl | H | — |
| 12 | B.1.b | 2 | H | 4-Cl | H | — |
| 13 | B.1.b | 2 | H | 3-Cl | H | — |
| 14 | B.1.b | 4 | H | 4-Br | H | — |
| 15 | B.1.b | 3 | H | 4-Br | H | — |
| 16 | B.1.b | 2 | H | 4-Br | H | — |
| 17 | B.1.a | 3 | H | 2-OCH$_3$ | H | — |
| 18 | B.1.a | 2 | H | 2-OCH$_3$ | H | (E)-2-butenedioate (1:1) |
| 19 | B.1.c | 2 | H | 3-OCH$_3$ | H | (E)-2-butenedioate (1:1) |
| 20 | B.1.c | 3 | H | 3-OCH$_3$ | H | (E)-2-butenedioate (1:1) |
| 21 | B.1.c | 2 | H | 4-OCH$_3$ | H | — |
| 22 | B.1.c | 3 | H | 4-OCH$_3$ | H | — |
| 23 | B.1.c | 2 | H | 3-OCH$_3$ | 4-OCH$_3$ | — |
| 24 | B.1.c | 3 | H | 3-OCH$_3$ | 4-OCH$_3$ | — |
| 25 | B.1.c | 3 | H | 4-F | H | — |
| 26 | B.1.c | 4 | H | 4-OCH$_3$ | H | — |
| 27 | B.1.d | 3 | H | 3-CF$_3$ | H | — |
| 28 | B.1.d | 5 | H | 2-F | H | — |
| 29 | B.1.c | 5 | H | 4-OCH$_3$ | H | — |
| 30 | B.1.d | 5 | H | 2-OCH$_3$ | H | — |
| 31 | B.1.d | 4 | H | 3-OCH$_3$ | H | (E)-2-butenedioate (1:1) |
| 32 | B.1.c | 2 | H | 2-F | H | (E)-2-butenedioate (2:3) |
| 33 | B.1.c | 3 | H | 2-F | H | — |
| 34 | B.1.c | 4 | H | 4-F | H | — |
| 35 | B.1.c | 4 | H | 2-F | H | — |
| 36 | B.1.d | 5 | H | 3-OCH$_3$ | H | (E)-2-butenedioate (2:1) |
| 37 | B.1.d | 4 | H | 3-CF$_3$ | H | (E)-2-butenedioate (2:3) |
| 38 | B.1.d | 5 | H | 3-CF$_3$ | H | (E)-2-butenedioate (1:1) |
| 39 | B.1.d | 2 | H | 3-CF$_3$ | H | (E)-2-butenedioate (1:1) |
| 40 | B.1.d | 2 | H | 4-CH$_3$ | H | — |
| 41 | B.2 | 2 | 6-Cl | 3-Cl | 4-Cl | — |
| 42 | B.2 | 4 | 6-OCH$_3$ | 3-Cl | 4-Cl | (E)-2-butenedioate (1:1) |
| 43 | B.1.c | 2 | H | 4-F | H | — |
| 44 | B.1.d | 2 | H | 2-CH$_3$ | 6-CH$_3$ | — |
| 45 | B.4 | 3 | 6-CH$_3$ | 3-Cl | 4-Cl | — |
| 46 | B.1.d | 3 | H | 2-CH$_3$ | 6-CH$_3$ | — |
| 47 | B.1.d | 4 | H | 2-CH$_3$ | 6-CH$_3$ | — |
| 48 | B.1.d | 5 | H | 2-CH$_3$ | 6-CH$_3$ | — |
| 49 | B.1.d | 2 | H | 2-CH$_3$ | 5-CH$_3$ | — |
| 50 | B.1.d | 4 | H | 2-CH$_3$ | 5-CH$_3$ | — |
| 51 | B.1.e | 2 | 6-OCH$_3$ | 3-Cl | 4-Cl | 2 HCl |
| 52 | B.1.e | 4 | 6-CH$_3$ | 3-Cl | 4-Cl | — |
| 53 | B.3 | 2 | 6-CH$_3$ | 3-Cl | 4-Cl | — |
| 54 | B.1.d | 5 | H | 4-F | H | — |
| 55 | B.1.d | 5 | H | 2-CH$_3$ | 5-CH$_3$ | — |
| 56 | B.1.e | 4 | 6-Cl | 3-Cl | 4-Cl | — |
| 57 | B.1.e | 5 | 6-F | 3-Cl | 4-Cl | — |
| 58 | B.1.d | 3 | H | 4-CH$_3$ | H | — |
| 59 | B.1.d | 5 | H | 4-CH$_3$ | H | — |

TABLE 1-continued

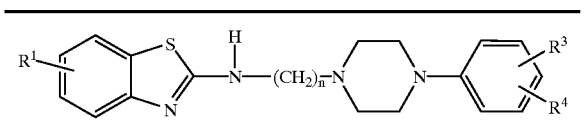

| Comp. No. | Ex. No. | n | R¹ | R³ | R⁴ | Physical data |
|---|---|---|---|---|---|---|
| 60 | B.1.d | 4 | H | 4-CH₃ | H | — |
| 61 | B.1.d | 2 | H | 2-CH₃ | 3-CH₃ | — |
| 62 | B.1.e | 5 | 6-CH₃ | 3-Cl | 4-Cl | — |
| 63 | B.1.e | 5 | 6-OCH₃ | 3-Cl | 4-Cl | — |
| 64 | B.1.d | 3 | H | 2-CH₃ | 3-CH₃ | — |
| 65 | B.1.d | 4 | H | 2-CH₃ | 3-CH₃ | — |
| 66 | B.1.e | 5 | 6-Cl | 3-Cl | 4-Cl | — |
| 67 | B.1.e | 4 | 6-F | 3-Cl | 4-Cl | — |
| 68 | B.1.d | 3 | H | 2-OCH₃ | 4-OCH₃ | — |
| 69 | B.1.d | 5 | H | 2-CH₃ | 3-CH₃ | — |
| 70 | B.1.d | 4 | H | 3-CH₃ | H | — |
| 71 | B.1.d | 2 | H | 2-OCH₃ | 4-OCH₃ | — |
| 72 | B.4 | 3 | 6-OCH₃ | 3-Cl | 4-Cl | 2 HCl |
| 73 | B.1.d | 4 | H | 2-OCH₃ | H | (E)-2-butenedioate (1:1) |
| 74 | B.1.d | 3 | H | 3-CH₃ | H | (E)-2-butenedioate (1:1) |
| 75 | B.1.d | 2 | H | 3-CH₃ | 4-CH₃ | — |
| 76 | B.1.d | 3 | H | 3-CH₃ | 4-CH₃ | — |
| 77 | B.1.d | 4 | H | 3-CH₃ | 4-CH₃ | — |
| 78 | B.3 | 2 | 7-F | 3-Cl | 4-Cl | — |
| 79 | B.1.d | 5 | H | 2-Cl | H | (E)-2-butenedioate (2:3) |
| 80 | B.1.e | 3 | 6-Cl | 3-Cl | 4-Cl | — |
| 81 | B.1.e | 3 | 6-F | 3-Cl | 4-Cl | — |
| 82 | B.1.d | 4 | H | 2-Cl | H | — |
| 83 | B.1.d | 5 | H | 3-CH₃ | 4-CH₃ | — |
| 84 | B.1.d | 2 | H | 2-Cl | H | (E)-2-butenedioate (1:1) |
| 85 | B.1.d | 3 | H | 2-Cl | H | — |
| 86 | B.1.d | 5 | H | 3-CH₃ | H | — |
| 87 | B.1.d | 2 | H | 3-CH₃ | H | (E)-2-butenedioate (1:1) |
| 88 | B.1.d | 3 | H | 2-CH₃ | 5-CH₃ | — |
| 89 | B.1.d | 3 | H | 2-CH₃ | 4-CH₃ | — |
| 90 | B.1.d | 2 | H | 2-CH₃ | H | — |
| 91 | B.1.d | 3 | H | 2-CH₃ | H | — |
| 92 | B.1.d | 4 | H | 2-CH₃ | H | — |
| 93 | B.1.d | 5 | H | 2-CH₃ | H | — |
| 122 | B.1.d | 2 | H | 2-CH₃ | 4-CH₃ | — |
| 123 | B.1.d | 4 | H | 2-CH₃ | 4-CH₃ | — |
| 124 | B.1.d | 5 | H | 2-CH₃ | 4-CH₃ | — |
| 125 | B.1.d | 3 | H | 4-NO₂ | H | — |
| 126 | B.8 | 2 | H | 4-Br | H | (E)-2-butenedioate (2:1) |
| 127 | B.8 | 2 | H | 4-Cl | H | — |
| 128 | B.1.e | 2 | H | 4-I | H | — |
| 129 | B.1.e | 2 | 6-OCH₃ | 4-Cl | H | (E)-2-butenedioate (2:1) |
| 130 | B.1.e | 2 | 6-F | 4-Cl | H | — |
| 131 | B.8 | 2 | H | 4-Cl | H | HBr (1:2) |
| 132 | B.8 | 2 | H | 4-Cl | H | ethanedioate (1:1) |
| 133 | B.8 | 2 | H | 4-Cl | H | (S)-hydroxybutene-dioate (1:1) |
| 134 | B.8 | 2 | H | 4-Cl | H | H₂O (1:2)/HCl (1:1) |
| 135 | B.8 | 2 | H | 4-Cl | H | (+)-[R-(R*,R*)]-2,3-dihydroxybutenedioate (1:1) |
| 136 | B.11 | 2 | 7-CH₃ | 4-Cl | H | — |
| 137 | B.11 | 2 | 5-Cl | 4-Cl | H | — |
| 138 | B.11 | 2 | 5-CH₃ | 4-Cl | H | — |
| 139 | B.11 | 2 | 5-OH | 4-Cl | H | — |
| 140 | B.11 | 2 | 6-OH | 4-Cl | H | HCl (1:3) |
| 141 | B.11 | 2 | 5-F | 4-Cl | H | — |
| 142 | B.11 | 2 | 4-F | 4-Cl | H | HCl (1:2) |
| 143 | B.10 | 2 | 4-OCH₃ | 4-Cl | H | HCl (1:2)/H₂O (1:1) |
| 144 | B.1.e | 2 | 6-CH₃ | 4-Cl | H | (E)-2-butenedioate (1:1) |
| 145 | B.1.e | 2 | 6-Cl | 4-Cl | H | — |

TABLE 1-continued

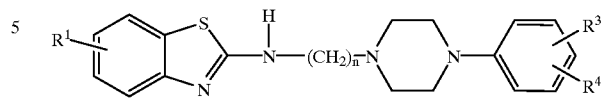

| Comp. No. | Ex. No. | n | R¹ | R³ | R⁴ | Physical data |
|---|---|---|---|---|---|---|
| 146 | B.11 | 2 | 4-Cl | 4-Cl | H | HCl (1:3) |
| 147 | B.11 | 2 | 4-CH₃ | 4-Cl | H | (E)-2-butenedioate (2:1) |

TABLE 2

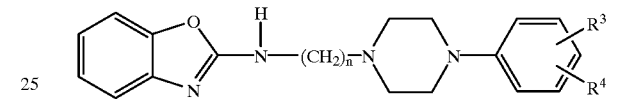

| Comp. No. | Ex. No. | n | R³ | R⁴ | Physical data |
|---|---|---|---|---|---|
| 94 | B.2 | 4 | 3-Cl | 4-Cl | — |
| 95 | B.2 | 5 | 3-Cl | 4-Cl | — |
| 96 | B.2 | 2 | 3-Cl | 4-Cl | — |
| 97 | B.2 | 3 | 3-Cl | 4-Cl | — |

TABLE 3

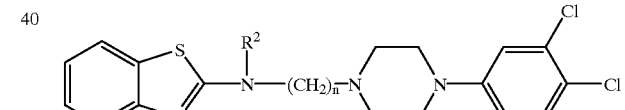

| Comp. No. | Ex. No. | n | R² | Physical data |
|---|---|---|---|---|
| 98 | B.6 | 2 | phenylcarbonyl | (E)-2-butenedioate (1:1) |
| 99 | B.6 | 3 | phenylcarbonyl | — |
| 100 | B.1.a | 3 | methyl | — |
| 101 | B.1.a | 2 | methyl | — |
| 102 | B.7 | 4 | methyl | — |
| 103 | B.5 | 3 | 1-butyl | (E)-2-butenedioate (2:1) |
| 104 | B.5 | 3 | phenylmethyl | (E)-2-butenedioate (1:1) |
| 105 | B.5 | 2 | phenylmethyl | (E)-2-butenedioate (2:1) |
| 106 | B.5 | 2 | phenylmethyl | (E)-2-butenedioate (1:1) |
| 107 | B.5 | 2 | 1-butyl | (E)-2-butenedioate (1:1) |
| 108 | B.5 | 4 | phenylmethyl | (E)-2-butenedioate (1:1) |
| 109 | B.5 | 4 | 1-butyl | (E)-2-butenedioate (2:1) |
| 110 | B.7 | 5 | methyl | (E)-2-butenedioate (1:1) |
| 111 | B.5 | 5 | 1-butyl | (E)-2-butenedioate (1:1) |
| 112 | B.5 | 5 | phenylmethyl | (E)-2-butenedioate (1:1) |
| 113 | B.12 | 3 | phenyl | (E)-2-butenedioate (1:1) |
| 114 | B.12 | 2 | phenyl | (E)-2-butenedioate (1:1) |
| 115 | B.7 | 4 | phenyl | (E)-2-butenedioate (2:1) |
| 116 | B.7 | 5 | phenyl | (E)-2-butenedioate (1:1) |
| 117 | B.9 | 2 | methyl | (E)-2-butenedioate (1:1) |

TABLE 4

Benzothiazole-NH-(CH₂)ₙ-piperazine-naphthalene structure

| Comp. No. | Ex. No. | n | Physical data |
|---|---|---|---|
| 118 | B.1.d | 4 | (E)-2-butenedioate (2:1) |
| 119 | B.1.d | 2 | (E)-2-butenedioate (1:1) |
| 120 | B.1.d | 3 | — |
| 121 | B.1.d | 5 | (E)-2-butenedioate (2:1) |

Table 5 lists both the experimental (column heading "exp") and theoretical (column heading "theor") elemental analysis values for carbon, hydrogen and nitrogen of the compounds as prepared in the experimental part hereinabove.

TABLE 5

| Comp No. | Carbon exp | Carbon theor | Hydrogen exp | Hydrogen theor | Nitrogen exp | Nitrogen theor |
|---|---|---|---|---|---|---|
| 3 | 56.04 | 57.01 | 5.33 | 5.26 | 12.92 | 13.30 |
| 11 | 62.11 | 62.90 | 6.11 | 6.28 | 13.65 | 13.97 |
| 12 | 61.25 | 61.20 | 5.59 | 5.68 | 15.05 | 15.02 |
| 13 | 61.25 | 61.20 | 5.61 | 5.68 | 15.01 | 15.02 |
| 16 | 54.56 | 54.68 | 4.80 | 5.07 | 13.32 | 13.42 |
| 17 | 65.25 | 65.94 | 6.88 | 6.85 | 14.54 | 14.65 |
| 19 | 59.79 | 59.49 | 5.87 | 5.82 | 11.65 | 11.56 |
| 20 | 59.80 | 60.22 | 5.85 | 6.06 | 11.09 | 11.24 |
| 21 | 65.31 | 65.19 | 6.44 | 6.56 | 15.21 | 15.20 |
| 22 | 66.03 | 65.94 | 7.02 | 6.85 | 14.76 | 14.65 |
| 23 | 62.98 | 63.29 | 6.47 | 6.58 | 14.06 | 14.06 |
| 24 | 63.90 | 64.05 | 6.99 | 6.84 | 13.52 | 13.58 |
| 25 | 64.74 | 64.84 | 6.30 | 6.26 | 15.09 | 15.12 |
| 26 | 66.52 | 66.63 | 7.23 | 7.12 | 14.10 | 14.13 |
| 28 | 65.99 | 66.30 | 6.85 | 6.83 | 13.97 | 14.06 |
| 29 | 67.24 | 67.28 | 7.83 | 7.36 | 13.75 | 13.65 |
| 30 | 67.28 | 67.28 | 7.41 | 7.36 | 13.67 | 13.65 |
| 31 | 61.01 | 60.92 | 6.31 | 6.29 | 11.07 | 10.93 |
| 32 | 56.42 | 56.59 | 5.10 | 5.13 | 10.33 | 10.56 |
| 33 | 64.51 | 64.84 | 5.96 | 6.26 | 14.90 | 15.12 |
| 34 | 65.54 | 65.60 | 6.50 | 6.55 | 14.53 | 14.57 |
| 35 | 64.98 | 65.60 | 6.52 | 6.55 | 14.46 | 14.57 |
| 36 | 63.98 | 64.08 | 6.91 | 6.88 | 12.13 | 11.96 |
| 37 | 55.29 | 55.26 | 5.14 | 5.13 | 9.24 | 9.21 |
| 38 | 57.44 | 57.44 | 5.62 | 5.53 | 10.04 | 9.92 |
| 39 | 54.89 | 55.17 | 4.70 | 4.82 | 10.56 | 10.72 |
| 40 | 68.29 | 68.15 | 6.92 | 6.86 | 16.08 | 15.89 |
| 41 | 51.37 | 51.65 | 4.08 | 4.33 | 12.54 | 12.68 |
| 42 | 53.40 | 53.70 | 5.27 | 5.20 | 9.33 | 9.63 |
| 43 | 63.77 | 64.02 | 5.98 | 5.94 | 15.48 | 15.72 |
| 44 | 68.49 | 68.82 | 7.07 | 7.15 | 15.21 | 15.29 |
| 45 | 58.05 | 57.93 | 5.43 | 5.56 | 12.83 | 12.87 |
| 46 | 69.16 | 69.44 | 7.28 | 7.42 | 14.83 | 14.72 |
| 47 | 69.87 | 70.01 | 7.59 | 7.66 | 14.18 | 14.20 |
| 48 | 70.39 | 70.55 | 7.98 | 7.89 | 13.70 | 13.71 |
| 50 | 69.69 | 70.01 | 7.63 | 7.66 | 14.24 | 14.20 |
| 51 | 47.02 | 47.07 | 4.52 | 4.74 | 10.83 | 10.98 |
| 52 | 58.76 | 58.79 | 5.84 | 5.83 | 12.44 | 12.47 |
| 53 | 56.97 | 57.01 | 5.14 | 5.26 | 13.26 | 13.30 |
| 54 | 64.62 | 66.30 | 6.73 | 6.83 | 13.95 | 14.06 |
| 55 | 70.57 | 70.55 | 8.19 | 7.89 | 13.77 | 13.71 |
| 56 | 53.47 | 53.68 | 4.97 | 4.93 | 11.93 | 11.92 |
| 57 | 56.63 | 56.53 | 5.32 | 5.39 | 11.97 | 11.99 |
| 58 | 68.44 | 68.82 | 7.31 | 7.15 | 15.48 | 15.29 |
| 59 | 69.77 | 70.01 | 7.53 | 7.66 | 14.03 | 14.20 |
| 60 | 69.41 | 69.44 | 7.48 | 7.42 | 14.61 | 14.72 |
| 61 | 68.57 | 68.82 | 7.08 | 7.15 | 14.90 | 15.29 |
| 62 | 59.39 | 59.60 | 5.95 | 6.09 | 11.95 | 12.09 |
| 63 | 57.61 | 57.62 | 6.06 | 5.89 | 11.68 | 11.69 |
| 64 | 69.41 | 69.44 | 7.37 | 7.42 | 14.51 | 14.72 |
| 65 | 69.72 | 70.01 | 7.62 | 7.66 | 14.42 | 14.20 |
| 66 | 54.65 | 54.61 | 5.20 | 5.21 | 11.50 | 11.58 |
| 67 | 55.26 | 55.63 | 4.96 | 5.11 | 12.19 | 12.36 |
| 68 | 63.43 | 64.05 | 6.88 | 6.84 | 13.73 | 13.58 |
| 69 | 69.50 | 70.55 | 7.78 | 7.89 | 13.72 | 13.71 |
| 70 | 68.94 | 69.44 | 7.74 | 7.42 | 15.02 | 14.72 |
| 71 | 63.44 | 63.29 | 6.58 | 6.58 | 14.08 | 14.06 |
| 72 | 48.04 | 48.10 | 4.96 | 5.00 | 10.51 | 10.69 |
| 73 | 61.03 | 60.92 | 6.53 | 6.29 | 10.80 | 10.93 |
| 74 | 62.21 | 62.22 | 6.15 | 6.27 | 11.51 | 11.61 |
| 75 | 67.90 | 68.82 | 7.13 | 7.15 | 15.10 | 15.29 |
| 76 | 69.15 | 69.44 | 7.23 | 7.42 | 14.72 | 14.72 |
| 77 | 68.57 | 70.01 | 7.66 | 7.66 | 13.89 | 14.20 |
| 78 | 53.33 | 53.65 | 4.89 | 4.50 | 13.09 | 13.17 |
| 80 | 52.54 | 52.70 | 4.41 | 4.64 | 12.28 | 12.29 |
| 81 | 54.83 | 54.67 | 5.04 | 4.82 | 12.85 | 12.75 |
| 83 | 70.58 | 70.55 | 7.96 | 7.89 | 13.88 | 13.71 |
| 84 | 55.94 | 56.49 | 5.03 | 5.15 | 11.20 | 11.46 |
| 85 | 62.26 | 62.08 | 5.93 | 5.99 | 14.54 | 14.48 |
| 86 | 69.74 | 70.01 | 7.67 | 7.66 | 14.10 | 14.20 |
| 88 | 67.75 | 69.44 | 7.19 | 7.42 | 14.05 | 14.72 |
| 94 | 59.95 | 60.15 | 5.75 | 5.77 | 13.34 | 13.36 |
| 95 | 60.62 | 60.97 | 6.16 | 6.05 | 12.80 | 12.93 |
| 96 | 58.43 | 58.32 | 5.19 | 5.15 | 14.58 | 14.32 |
| 97 | 59.48 | 59.27 | 5.44 | 5.47 | 14.04 | 13.82 |
| 98 | 57.06 | 57.42 | 4.33 | 4.50 | 8.76 | 8.93 |
| 99 | 61.59 | 61.71 | 5.05 | 4.99 | 10.62 | 10.66 |
| 100 | 57.82 | 57.93 | 5.44 | 5.56 | 12.83 | 12.87 |
| 101 | 57.02 | 57.01 | 5.01 | 5.26 | 13.21 | 13.30 |
| 102 | 58.64 | 58.79 | 5.85 | 5.83 | 12.34 | 12.47 |
| 103 | 58.28 | 58.31 | 6.01 | 6.02 | 10.35 | 10.46 |
| 104 | 59.32 | 59.33 | 5.27 | 5.14 | 8.94 | 8.93 |
| 105 | 60.33 | 60.54 | 5.09 | 5.08 | 10.05 | 10.09 |
| 106 | 58.75 | 58.73 | 4.92 | 4.93 | 8.93 | 9.13 |
| 107 | 55.82 | 55.96 | 5.41 | 5.57 | 9.58 | 9.67 |
| 108 | 59.88 | 59.90 | 5.36 | 5.34 | 8.71 | 8.73 |
| 109 | 58.64 | 59.01 | 6.29 | 6.24 | 10.13 | 10.19 |
| 110 | 56.17 | 55.96 | 5.66 | 5.57 | 9.73 | 9.67 |
| 111 | 58.10 | 57.97 | 6.07 | 6.16 | 8.99 | 9.01 |
| 112 | 60.32 | 60.45 | 5.45 | 5.53 | 8.32 | 8.55 |
| 126 | 52.68 | 53.06 | 4.74 | 4.88 | 11.62 | 11.78 |
| 128 | 49.59 | 49.14 | 4.55 | 4.56 | 12.52 | 12.07 |
| 129 | 56.84 | 57.32 | 5.35 | 5.47 | 12 | 12.15 |
| 135 | 52.01 | 52.82 | 5.25 | 5.2 | 10.58 | 10.71 |
| 136 | 60.94 | 62.08 | 5.86 | 5.99 | 13.96 | 14.48 |
| 137 | 55.9 | 56.02 | 4.89 | 4.95 | 13.67 | 13.75 |
| 138 | 61.74 | 62.08 | 5.96 | 5.99 | 14.26 | 14.48 |
| 139 | 58.56 | 58.68 | 5.52 | 5.44 | 14.62 | 14.41 |
| 141 | 58.28 | 58.38 | 5.13 | 5.16 | 14.22 | 14.33 |
| 142 | 48.88 | 49.2 | 4.7 | 4.78 | 12.37 | 12.08 |
| 145 | 56 | 56.02 | 5.07 | 4.95 | 13.87 | 13.75 |
| 146 | 43.36 | 45.39 | 4.85 | 4.61 | 10.11 | 8.36 |
| 147 | 58.93 | 59.38 | 5.75 | 5.66 | 12.35 | 12.59 |

C. Pharmacological Example

EXAMPLE C.1

In vitro binding affinity for dopamine $D_4$ receptor

The interaction of the compounds of formula (I) with the dopamine $D_4$ receptors was assessed in in vitro radioligand binding experiments. A low concentration of $^3$H-spiperone with a high binding affinity for the dopamine $D_4$ receptor was incubated with a sample of a membrane preparation of transfected Chinese Hamster Ovary (CHO) cells which express cloned human $D_4$ receptors (Receptor Biology, Maryland, USA) in a buffered medium. When equilibrium of binding was reached, the receptor bound radioactivity was separated from the non-bound radioactivity, and the receptor bound activity was counted. The interaction of the test compounds, added to the incubation mixture in various concentrations, with the dopamine $D_4$ receptor was assessed in competition binding experiments as described by Schotte et al. (Psychopharmacology, 1996, 124, 57–73). The compounds with number 2 to 4, 6, 8 to 19, 21, 23, 25, 100, 101, 106, 117 to 126, 119, 128 to 130, 134 and 136 to 147 had a $pIC_{50}$ greater than or equal to 7 ($pIC_{50}$ is defined as -log $IC_{50}$ wherein $IC_{50}$ is the concentration of the test compound causing an inhibition of 50% of the dopamine $D_4$ receptors). The remaining compounds which were prepared in the experimental part were either not tested or had a $pIC_{50}$ of less than 7.

D. Composition Examples

"Active ingredient" (A.I.) as used throughout these examples relates to a compound of formula (I), a pharmaceutically acceptable addition salt or a stereochemically isomeric form thereof.

EXAMPLE D.1

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE D.2

Film-coated tablets

Preparation of tablet core: A mixture of A.I. (100 g), lactose (570 g) and starch (200 g) is mixed well and thereafter humidified with a solution of sodium dodecyl sulfate (5 g) and polyvinylpyrrolidone (10 g) in water (200 ml). The wet powder mixture is sieved, dried and sieved again. Then there are added microcrystalline cellulose (100 g) and hydrogenated vegetable oil (15 g). The whole is mixed well and compressed into tablets, giving 10.000 tablets, each comprising 10 mg of the active ingredient. Coating To a solution of methyl cellulose (10 g) in denaturated ethanol (75 ml) there is added a solution of ethyl cellulose (5 g) in dichloromethane (150 ml). Then there are added dichloromethane (75 ml) and 1,2,3-propanetriol (2.5 ml). Polyethylene glycol (10 g) is molten and dissolved in dichloromethane (75 ml). The latter solution is added to the former and then there are added magnesium octadecanoate (2.5 g), polyvinylpyrrolidone (5 g) and concentrated colour suspension (30 ml) and the whole is homogenated. The tablet cores are coated with the thus obtained mixture in a coating apparatus.

EXAMPLE D.3

Oral solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.4

Injectable solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

What is claimed is:

1. A compound having the formula

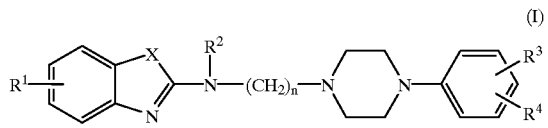

a N-oxide form, a pharmaceutically acceptable acid addition salt or a stereochemically isomeric form thereof, wherein X is O or S;

n is 2, 3, 4 or 5;

$R^1$ is hydrogen, $C_{1-6}$alkyl, $C_{1-6}$ alkyloxy or halo;

$R^2$ is hydrogen, $C_{1-6}$alkyl, phenyl, phenyl$C_{1-6}$alkyl or phenylcarbonyl;

$R^3$ and $R^4$ each independently are selected from hydrogen, halo, nitro, $C_{1-6}$alkyl, $C_{1-6}$ alkyloxy, halo$C_{1-6}$alkyl, aminosulfonyl, mono- or di($C_{1-4}$alkyl) aminosulfonyl; or $R^3$ and $R^4$ may also be taken together to form a bivalent radical of formula —CH=CH—CH=CH—.

2. A compound according to claim 1 wherein n is 2, 3 or 4.

3. A compound according to claim 1 wherein X is S and $R^2$ is hydrogen, $C_{1-6}$alkyl, phenyl or phenyl$C_{1-6}$alkyl.

4. A compound according to claim 1 wherein $R^2$ and $R^3$ are hydrogen and $R^4$ is chloro.

5. A compound according to claim 1 wherein the compound is

N-[2-[4-(3,4-dichlorophenyl)-1-piperazinyl]ethyl]-2-benzothiazolamine;

N-[2-(4-phenyl-1-piperazinyl)ethyl]-2-benzothiazolamine;

N-[2-[4-(4-chlorophenyl)-1-piperazinyl]ethyl]-2-benzothiazolamine;

N-[2-[4-(4-bromophenyl)-1-piperazinyl]ethyl]-2-benzothiazolamine; a N-oxide, a stereoisomeric form or a pharmaceutically acceptable acid addition salt thereof.

6. A pharmaceutical composition comprising a pharmaceutically acceptable carrier and, as active ingredient, an effective dopamine $D_4$ receptor antagonizing amount of a compound as described in claim 1.

7. A process of preparing a pharmaceutical composition comprising intimately mixing a pharmaceutically acceptable carrier with an effective dopamine $D_4$ receptor antagonizing amount of a compound as described in claim 1.

8. A process of preparing a compound as described in claim 1, characterized by a) N-alkylating an intermediate of formula (III)

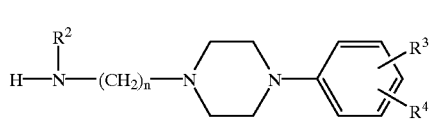
(III)

wherein n and $R^2$ to $R^4$ are defined as in claim 1, with an intermediate of formula (II)

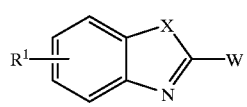
(II)

wherein W represents an appropriate reactive leaving group, and X and $R^1$ are defined as in claim 1, in a reaction-inert solvent, optionally in the presence of a suitable base, and optionally in the presence of a catalyst;

b) reacting an intermediate of formula (III)

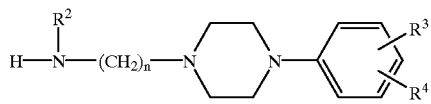
(III)

wherein n and $R^2$ to $R^4$ are defined as in claim 1, with an intermediate of formula (IV)

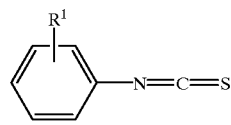
(IV)

wherein $R^1$ is defined as in claim 1, in a reaction-inert solvent and in the presence of thionylchloride; thus forming a compound of formula (I-a)

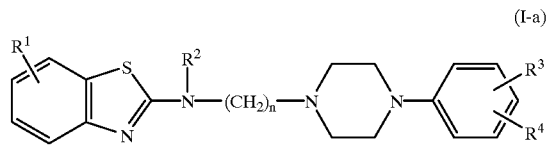
(I-a)

c) N-alkylating an intermediate of formula (VI)

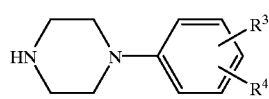
(VI)

wherein $R^3$ and $R^4$ are defined as in claim 1, with an intermediate of formula (VII)

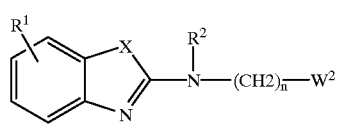
(VII)

wherein $R^1$, $R^2$, n and X are defined as in claim 1 and $W^2$ is an appropriate leaving group, in a reaction-inert solvent;

d) N-alkylating an intermediate of formula (XV)

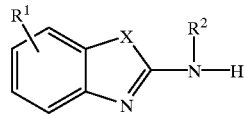
(XV)

wherein X, $R^1$ and $R^2$ are defined as in claim 1, with an intermediate of formula (XVI)

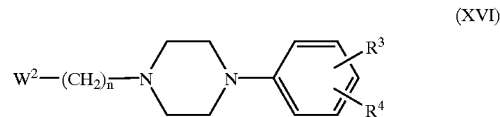
(XVI)

wherein n, $R^3$ and $R^4$ are defined as in claim 1 and $W^2$ is an appropriate leaving group, in a reaction-inert solvent, in the presence of a suitable base;

e) and further, if desired, converting the compounds of formula (I), into a therapeutically active non-toxic acid addition salt by treatment with an acid, or conversely, converting the acid addition salt form into the free base by treatment with alkali; and, if desired, preparing stereochemically isomeric forms or N-oxides thereof.

9. A method of treating a warm-blooded animal suffering from a psychotic disorder comprising administering to the warm-blooded animal a dopamine $D_4$ receptor antagonizing amount of the compound of claim 1.

10. The method of claim 9, wherein the pyschotic disorder is schizophrenia.

* * * * *